United States Patent [19]
Okumura et al.

[11] Patent Number: 5,636,258
[45] Date of Patent: Jun. 3, 1997

[54] IN-SITU TEMPERATURE MEASUREMENT USING X-RAY DIFFRACTION

[75] Inventors: Katsuya Okumura, Poughkeepsie, N.Y.; James G. Ryan, Newtown, Conn.; Gregory B. Stephenson, Lisle, Ill.; Hans-Joerg Timme, Wappingers Falls, N.Y.

[73] Assignees: Siemens Aktiengesellschaft, Munich, Germany; International Business Machines Corporation, Armonk, N.Y.; Kabushiki Kaisha Toshiba, Kanagawa-ken, Japan

[21] Appl. No.: 554,209

[22] Filed: Oct. 24, 1995

[51] Int. Cl.⁶ .................................. G01N 23/207
[52] U.S. Cl. ............................... 378/73; 378/71
[58] Field of Search .......................... 378/73, 71

[56] References Cited

U.S. PATENT DOCUMENTS

| | | | |
|---|---|---|---|
| 4,821,301 | 4/1989 | Cocks et al. | 378/70 |
| 5,021,980 | 6/1991 | Poenisch et al. | 364/557 |
| 5,046,077 | 9/1991 | Murayama | 378/73 |
| 5,167,452 | 12/1992 | Amith et al. | 374/121 |
| 5,208,643 | 5/1993 | Fair | 356/43 |
| 5,213,985 | 5/1993 | Sandroff et al. | 437/8 |
| 5,249,865 | 10/1993 | Paranjpe et al. | 374/161 |
| 5,258,602 | 11/1993 | Naselli et al. | 219/497 |

*Primary Examiner*—Craig E. Church
*Attorney, Agent, or Firm*—Donald B. Paschburg

[57] ABSTRACT

A non-contact in-situ temperature measurement apparatus for a single crystal substrate such as a semiconductor wafer using X-ray diffraction. Utilizing the Bragg condition for X-ray diffraction, the lattice constant of the semiconductor substrate can be determined either by measuring the diffraction angle for a monochromatic X-ray (monochromatic approach) or by measuring the wavelength of an X-ray diffracted with a certain scattering angle (polychromatic approach). The lattice constant, as a well-known function of temperature, is finally converted into the temperature of the semiconductor substrate.

13 Claims, 3 Drawing Sheets

IN-SITU TEMPERATURE MEASUREMENT USING X-RAY DIFFRACTION

BACKGROUND OF THE INVENTION

1. Field of the Invention

The present invention generally relates to in-situ temperature measurement in semiconductor processing using X-ray diffraction and, more particularly, to in-situ temperature measurement conducted by measuring single crystal substrate (e.g., semiconductor wafer) lattice parameters by X-ray diffraction.

2. Description of the Related Art

Accurate temperature control is required in many semiconductor processes such as rapid thermal processing (RTP), annealing, oxidation, nitridation, and chemical vapor deposition (CVD). It is also required for processes such as plasma enhanced chemical vapor deposition (PECVD), physical vapor deposition (PVD), and reactive ion etching (RIE). Temperature measurement during semiconductor processing, however, is very difficult because it usually requires the use of contact methods such as thermocouples. If non-contact in-situ measurement is required, then methods such as optical pyrometry are often used. Optical pyrometry has several drawbacks including inaccuracy at lower temperature ranges, since it is dependent on the measured wavelength, and dependence on wafer (backside) emissivity or film structure on the substrate.

SUMMARY OF THE INVENTION

It is therefore an object of the present invention to provide an improved method and apparatus for in-situ contactless temperature measurement in semiconductor processing.

According to the invention, there is provided an in-situ non-contact temperature measurement for single crystal semiconductor substrates like, for example, Si, Ge, or GaAs wafers. Although we speak of semiconductor substrates or wafers, it is understood that such substrates or wafers may be coated with certain films or structures that usually occur during semiconductor processing. It is based on the measurement of lattice parameters by means of X-ray diffraction. Lattice parameters, like the so-called lattice constant, are temperature dependent. See, for example, N. W. Ashcroft and N. D. Mermin, *Solid State Physics*, Saunders, Philadelphia, 1976. Due to precise thermal expansion studies and measurements, the lattice parameters as a function of the temperature are well known for many materials. See, for example, R. S. Krishnan, R. Srinivasan, and S. Devanarayanan, *Thermal Expansion of Crystals*, Pergamon Press, Oxford, 1979.

The invention makes it possible to precisely measure the single crystal semiconductor substrate temperature during processing without contacting the semiconductor. More specifically, it allows in-situ process temperature calibration and control. This invention applies to all kind of semiconductor processing or manufacturing equipment in which the semiconductor (substrate) temperature is an important process parameter (i.e., thermal processors).

To achieve these and other advantages and in accordance with the purpose of the invention, as embodied and broadly described, the invention provides a non-contact in-situ temperature measurement apparatus for a semiconductor wafer, comprising a process chamber housing the semiconductor wafer, an incident X-ray source communicating with the wafer through a communication means in the process chamber, means for receiving reflected X-rays from the wafer, and means for determining the lattice constant of the wafer based on the received reflected X-ray so that the temperature of the wafer may be obtained.

In the practice of the invention, a method of non-contact in-situ temperature measurement for a semiconductor wafer comprises the steps of providing a single crystal semiconductor (e.g., Si or GAAS) wafer in a process chamber, providing an incident X-ray source communicating with the wafer in the process chamber, receiving reflected X-rays from the wafer, determining the lattice constant of the wafer based on the received reflected X-ray, and obtaining the temperature of the wafer as determined by the lattice constant.

It is to be understood that both the foregoing general description and the following detailed description are exemplary and explanatory and are intended to provide further explanation of the invention as claimed.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE INVENTION

Figure 1:
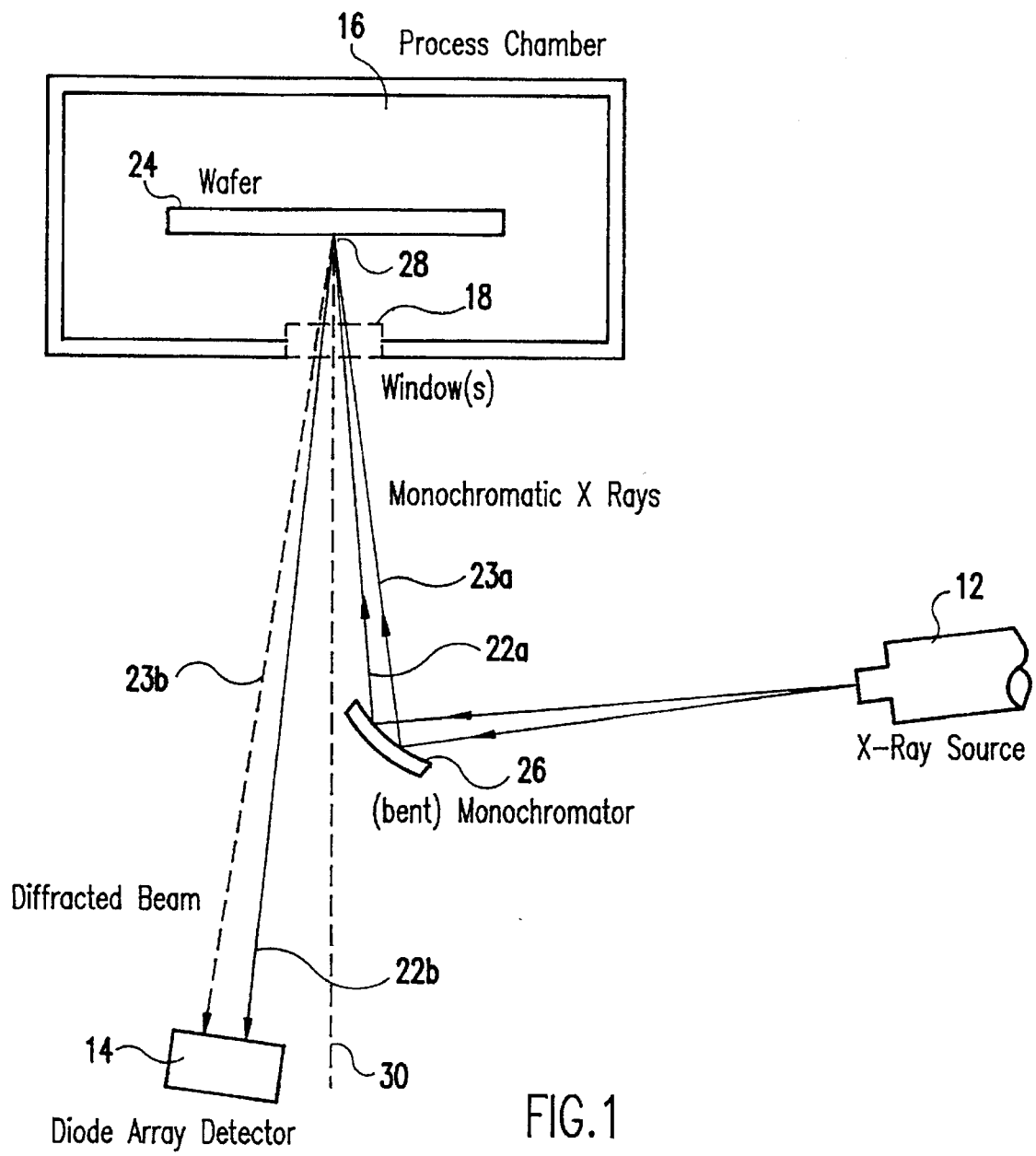
FIG. 1 is a schematic diagram of an in-situ temperature measurement apparatus in accordance with the present invention.

Referring now to the drawings, and more particularly to FIG. 1, there is shown an exemplary embodiment of an in-situ temperature measurement apparatus in accordance with the present invention. Generally, the X-ray source 12 and diode array detector 14 are located outside the process chamber 16 of a piece of semiconductor processing equipment. The incident X-ray beam (bundle of X-rays including, for example, 22a and 23a) and the single reflected X-ray, for example 22b or 23b, respectively, are coupled through one or more windows 18 to the process chamber 16. The windows 18 are made of a suitable material such as for example, beryllium. The X-ray diffraction can take place either on the backside, on the frontside, or at the edge of the semiconductor wafer 24.

Figure 2:
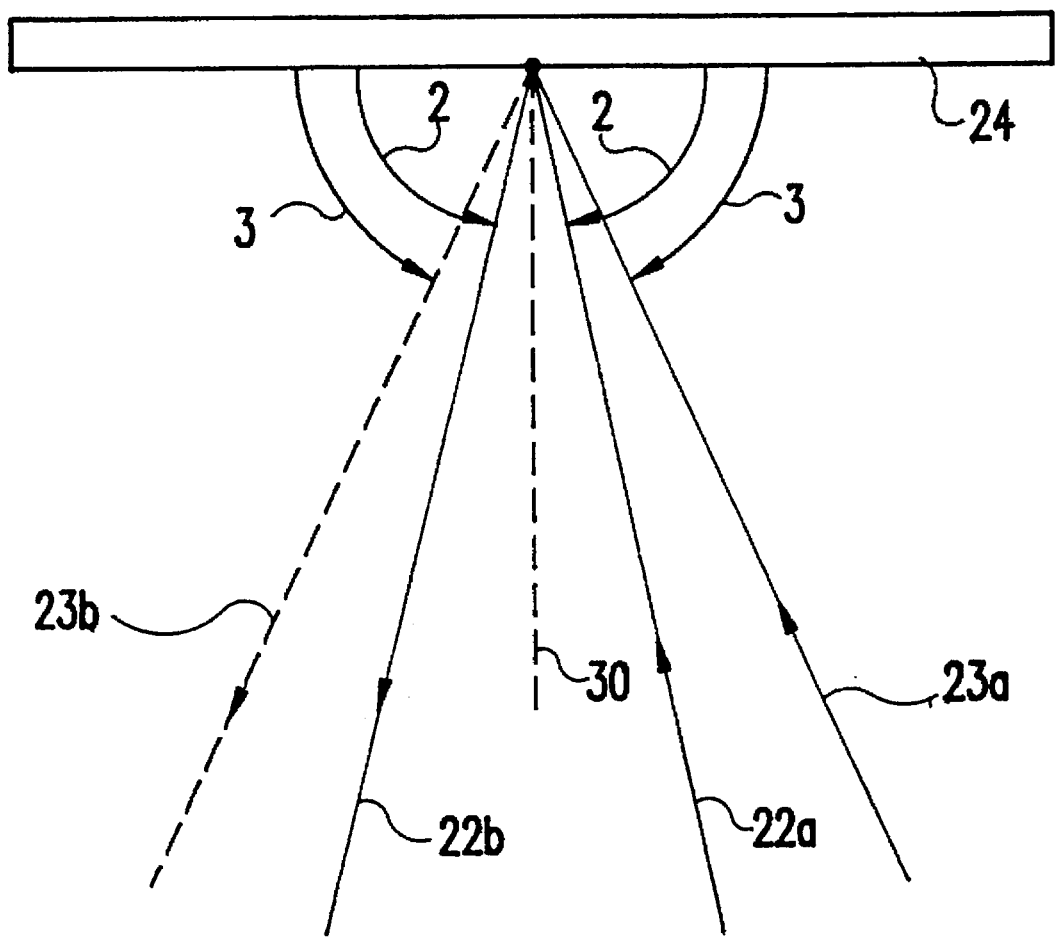
FIG. 2 is a schematic diagram illustrating the angles of the incident and reflected X-rays from the semiconductor wafer.

The X-ray source 12 may be a standard laboratory X-ray source that normally provides a divergent beam containing monochromatic emission lines superimposed on a polychromatic background. A monochromator may be used to select radiation of a particular wavelength. As a specific example, a bent monochromator 26, with one- or two-dimensional curvature, can be used to provide focused monochromatic X-rays. In FIG. 1, the dotted line 30 represents the symmetry axis of the X-ray source/detector unit consisting of source 12 and detector array 14. This axis should be perpendicular to the wafer (backside) surface for a (001) Si wafer, for example. The solid line 22b represents a reflected X-ray for some low temperature, say 20° C., while the dotted line 23b represents a reflected X-ray for some high temperature, say 1200° C. FIG. 2 shows, in more detail, the relationship of the incident and reflected X-rays. The angle 2 represents the diffraction angle θ for the incident X-ray 22a and the reflected X-ray 22b, while the angle 3 represents the diffraction angle θ for the incident X-ray 23a and the reflected X-ray 23b. Note that the total scattering angle of the X-ray is 2θ.

If monochromatic divergent or focused (convergent) beams are used, measurement of the temperature dependent Bragg angle θ(a(T)) or of the shift δθ(a(T))=θ(a(T_o))—θ(a(T_{ini})), respectively, will provide precise information on the lattice constant a(T) and hence, via thermal expansion relation, the substrate temperature T. In this case, a multi-channel photo diode array detector 14 is used to measure θ or δθ, respectively. A measurement of the diffraction angle θ requires information on the positioning of the wafer. In contrast, measurement of the shift δθ requires information on the initial wafer temperature $T_{ini}$ in order to determine θ(a($T_{ini}$))+δθ. The X-ray spot 28 on the semiconductor wafer 24 should be very small (~½m, for example) in order to allow precise measurement of the diffraction angle. Once the diffraction angle θ is determined, the lattice constant a can be obtained from the Bragg condition. The substrate temperature T can be calculated from the thermal expansion relationship by inverting the function a(T).

If, on the other hand, collimated polychromatic X-rays are used, it is necessary to measure the wavelength λ(a(T)) or the shift of wavelength δλ(a(T))=λ(a(T))—λ(a($T_{ini}$)), respectively, of the X-ray beam that is reflected under a fixed Bragg angle (θ=constant). Note that for elastic scattering of X-rays, the wavelength of the diffracted beam equals the wavelength of the incident beam, so that any δλ will be caused by a shift, δa, of a. In practice, it is more difficult to measure shifts δλ than shifts δθ of diffracted X-ray beams.

During thermal processing, changes in the wafer position might occur. Such changes may change the position of the single crystal substrate 24 with respect to the X-ray source 12 and detector array 14. As a consequence, shifts δθ or δλ, respectively, will occur which are not related to thermal expansion of the semiconductor lattice and hence disturb or even spoil the information on substrate temperature. In addition, even without such thermal effects, the substrate position might vary due to initially bent or warped wafers.

Therefore, one must precisely register the wafer position or single crystal orientation at or near the location where the X-ray beam diffraction occurs. The measured information can then be fed back to a position compensation means to either ensure accurate positioning of the semiconductor substrate 24 with respect to the X-ray source 12 and detector array 14 or to provide data correction. The position means may include fast mechanical adjustments within the X-ray source/detector unit or software algorithms for correction of measured δθ or δλ signals.

Figure 3:
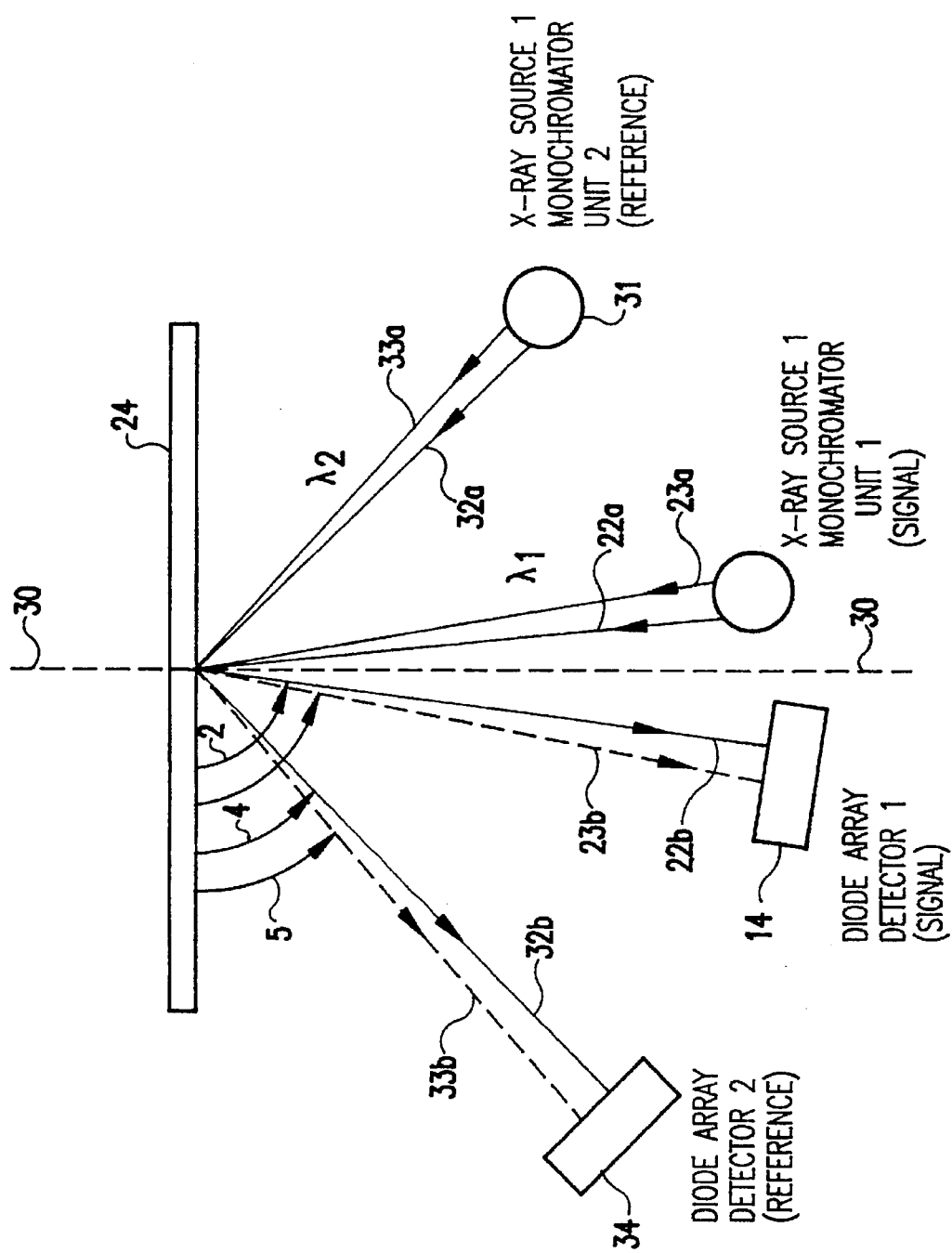
FIG. 3 is a schematic diagram showing a modification of the basic invention which compensates for a small tilt or misalignment of the wafer with respect to the X-ray source.

Measurement of wafer position or movement can be done, for example, by means of laser light. Another possibility, however, is to use a second diffracted X-ray beam as a reference beam, as shown in FIG. 3. In FIG. 3, a first X-ray source and monochromator (i.e., X-ray source 12 and monochromator 26 shown in FIG. 1) produces incident X-ray beams 22a and 23a at wavelength $\lambda_1$. A second reference X-ray source and monochromator 31 produces incident X-ray beams 32a and 33a at wavelength $\lambda_2$, where $\lambda_2<\lambda_1$. The incident beams 32a and 33a produce reflected X-rays 32b or 33b, depending again on the temperature of the wafer 24. The reflected X-ray beam 32b or 33b is received by the diode array reference detector 34. In FIG. 3, angle 4 is the diffraction angle θ for a low temperature, whereas angle 5 is the diffraction angel θ for a high temperature.

Consider, for example, the monochromatic approach with its measurement of shifts in the Bragg angle. The second reflection with a wavelength $\lambda_2<\lambda_1$ and a resulting Bragg angle $\theta_2<\theta_1$ can be chosen in such a way that shifts $\delta\theta_2$ are less sensitive to the thermal expansion δa of the semiconductor substrate than shift $\delta\theta_1$ for the main beam (with $\lambda_1$ and $\theta_1$). Because wafer bending or movement shifts $\theta_1$ and $\theta_2$ by exactly the same amount, shifts of $\theta_1$ with respect to $\theta_2$ contain information on thermal lattice expansion and thus substrate temperature. Note that it is possible to measure both angles, $\theta_1$ and $\theta_2$ (or shifts, $\delta\theta_1$ and $\delta\theta_2$) with the same precision.

The monochromatic embodiment of the invention will now be considered in greater detail. The method described below is both precise and flexible, and is applicable in the whole temperature regime of practical interest (i.e., from room temperature T=20° C. up to T=1200° C.). Note that most non-contact temperature measurement methods in semiconductor manufacturing are applicable or sensitive in a limited temperature range only.

In this embodiment, the monochromatic X-ray source 12 is used for the measurement of the lattice constant of (001) silicon substrate wafers. The monochromatic X-ray source 12 (which might be an X-ray tube with a monochromator) provides X-rays with a fixed wavelength λ incident at the sample over an appropriate range of angles, which include the Bragg angles θ(a(T)) for all temperatures of interest. The portion of this beam which makes the correct Bragg angle for the temperature of the sample will be reflected. This is shown by the solid line 22b in FIG. 1 and illustrated in more detail in FIG. 2. Measurement of the diffraction angle θ allows the determination of the lattice constant a by means of the Bragg condition and, finally, to determine the substrate temperature T via the thermal expansion relationship a=a(T).

In order to determine suitable reflections and corresponding values for λ and θ, the Laue or the equivalent Bragg condition for X-ray diffraction has to be used. In addition, information on the structure of the semiconductor crystal lattice and the corresponding reciprocal lattice is needed. Reflections or diffraction peaks are denoted by integer indices hkl belonging to corresponding vectors of the reciprocal lattice. Note that vectors of the reciprocal lattice are perpendicular to families of lattice planes in the original crystal lattice.

The X-ray diffraction by a crystal is described by the Laue condition $$K=k'-k \qquad (1)$$

where k and k' are the wave vectors of the incident and the diffracted beam, respectively. K is a vector of the reciprocal lattice. For elastic scattering, we have k'=k=2π/λ with k'=|k'| and k=|k|. As a consequence, both vectors k' and −k have the same angle φ with the vector K. Therefore, by multiplying Equation (1) with the vector K, one gets $K^2=2$ kKcosφ. Introducing the glancing angle (Bragg angle) θ between k or k' and the plane perpendicular to the vector K, this translates into $$K = 2k\sin\theta = \frac{4\pi}{\lambda}\sin\theta. \qquad (2)$$

Note that θ=π/2−φ. The total scattering angle between k and k' is given by 2θ.

Possible reflections are given by vectors K of the reciprocal lattice. Since lattices of the (monatomic) diamond or the (diatomic) zincblende structure are not Bravais lattices, they must be described as face-centered cubic lattices with a two point basis. The basis can be chosen as $d_1=0$, $d_2=(a/4)(e_x+e_y+e_z)$. The vectors $e_x$, $e_y$, $e_z$ are unit vectors along the cubic axes. As stated above, the parameter a is the lattice constant of the face-centered cubic lattice underlying the semiconductor lattice, which is a function of the temperature. At room temperature, a has values 5.43 Å, 5.66 Å, and 5.65 Å for Si, Ge, and GaAs, respectively. See Ashcroft et al., *Solid State Physics*.

The reciprocal lattice of the face-centered cubic (fcc) lattice with lattice constant a is body-centered cubic (bcc) with a cubic cell side $4\pi/a$. All reciprocal lattice vectors K can be parameterized by integer indices hkl according to $$K = \frac{2\pi}{a}(he_x + ke_y + le_z), \quad (3)$$

with lengths $$K = |K| = \frac{2\pi}{a}\sqrt{h^2+k^2+l^2}. \quad (4)$$

However, only for certain values of hkl will the vectors K given by Equation (3) be reciprocal lattice vectors (see below). If we introduce the spacing $$d_{hkl} = \frac{2\pi}{K} = \frac{a}{\sqrt{h^2+k^2+l^2}}, \quad (5)$$

Equation (2) takes the familiar form of the Bragg condition:

$$\lambda = 2d_{hkl} \sin\theta \quad (6)$$

Note that the order n that normally occurs in the Bragg condition is absorbed in the distance $d_{hkl}$ that is assigned to the reflection hkl.

We will consider only reflections hkl with reciprocal lattice vectors K in $e_z$ direction (e.g., with h=k=0). Because the bcc reciprocal lattice has a lattice constant of $4\pi/a$, there are only vectors with even l present. However, because the silicon lattice is described as a monatomic lattice with a basis, it is necessary to assign a geometrical structure factor to all points of the reciprocal bcc lattice. Thus, it turns out that only those vectors with l=4n, (n being an integer) give reflections. The other vectors with l=4n+2 have a geometrical structure factor of zero. See, again, Ashcroft et al., *Solid State Physics*. Note that the introduced n corresponds to the order of the diffraction at the family of <004> atomic planes in the silicon crystal, if the Bragg picture is used. Those planes have a distance of a/4. Hence, for this example, the diffraction Equation (6) is needed for reflections 004, 008, 0012 etc.

$$\lambda = \frac{2a}{l}\sin\theta, \quad (7)$$

for 001 reflections with l=4n, n an integer.

For a given l and cubic cell side a, Equation (7) relates the parameters $\lambda$ and $\theta$. In this example, the X-rays are monochromatic and small changes of the Bragg angle $\theta$ are measured to provide information on temperature dependent changes of the lattice parameter a. The quantity of interest is $$\frac{d\theta}{dT} = \frac{\partial\theta}{\partial a}\frac{da}{dT}. \quad (8)$$

From Krishnan et al., *Thermal Expansion of Crystals*, Table 5.1, we have for silicon $$\frac{da}{dT} = a(T_0)\alpha(T), \quad (9)$$

with $$\alpha(T) = A + B(T-T_0), \quad (10a)$$

and constants $$T_0 = 273K, \quad (10b)$$
$$A = 3.084 \times 10^{-6} K^{-1},$$
$$B = 1.957 \times 10^{-9} K^{-2}.$$

These parameters have been taken from the relation $$a(T) = a(T_0)[1 + A(T-T_0) + (B/2)(T-T_0)^2],$$

where the right hand side provides a polynomial least square fit to measured lattice constant data (obtained by X-ray diffraction in a temperature range from 293° to 970° K.). See, again, Krishnan et al., *Thermal Expansion of Crystals*. The lattice parameter changes from 5.4305 Å to 5.4579 Å as the temperature is increased from 20° C. to 1200° C. Note that according to Equations (9) and (10) a lattice parameter resolution of $2.7\times10^{-5}$ Å is necessary to achieve a substrate temperature resolution of ±1° C. for temperatures around 1000° C.

From Equation (7), one obtains $$\frac{\partial\theta}{\partial a} = -\frac{1}{a}\tan\theta. \quad (11)$$

Thus, $$\frac{d\theta}{dT} = -\frac{a(T_0)}{a(T)}\alpha(T)\tan\theta \approx -\alpha(T)\tan\theta. \quad (12)$$

Note that the temperature sensitivity in Equation (12) of the Bragg angle $\theta$ is larger for higher temperatures because of the increase of $\alpha$. However, going from room temperature to 1200° C., the sensitivity changes only by a factor of less than 2. The strongest impact on the sensitivity is provided by the reflection angle $\theta$ itself because of the increase of $\tan\theta$. Back reflection, with $\theta$ close to $\pi/2$ is most effective.

In order to estimate the possible temperature resolution, one must take the diode array detector 14 into consideration. A typical photo diode array detector has around 1024 channels, where individual channels are separated by a distance $\epsilon$. Let $\Delta$ denote the distance between wafer and detector, then for $\Delta \gg \epsilon$ the angular resolution is given by $$|\delta\theta_{min}| \approx \frac{\epsilon}{\Delta}, \quad (13)$$

assuming that the beam is converging to a spot on the sample that is smaller than $\epsilon$. Therefore, one obtains a temperature resolution of $$|\delta T_{min}| \approx \frac{1}{\alpha(T)}\frac{\epsilon}{\Delta\tan\theta}. \quad (14)$$

For best temperature resolution, the detector should have a small $\epsilon$ and should be placed a great distance $\Delta$ from the wafer. The glancing angle $\theta$ should be chosen as close to $\pi/2$ as the construction of the process chamber 16 and the X-ray source 12 and detector array 14 allow. The X-ray wavelength $\lambda$ follows from Equation (7) for a given reflection 001. A setup with $\epsilon = 1/20$ mm, $\Delta = 1$ m, and $\tan\theta = 10$ yields $$|\delta T_{min}| = 1K \text{ for } T = 1000° C., \text{ and} \quad (15)$$

$$|\delta T_{min}| = 1.6K \text{ for } T = 20° C.$$

For any chosen reflection 00l, the wavelength $\lambda$ and the diffraction angle $\theta$ must obey the Bragg Equations (6) or (7). This provides an upper limit to the X-ray wavelength: $\lambda \leq 2 d_{00l}$. In order to get the highest temperature resolution, $\lambda$ should be chosen as close to its upper limit as possible (back reflection). For silicon, one might use one of the following characteristic lines, for example:

a) Iridium $L_{\alpha 1}$ with $\lambda=1.3513$ Å for 008 with 2 $d_{008}=2a/8=1.3576$ Å. From Equation (6) it follows that $\theta=84.5°$ with $\tan\theta=10.3$.

b) Niobium $K_{\beta 1}$ with $\lambda=0.6658$ Å for 0016 with 2 $d_{0016}=2a/16=0.6788$ Å. From Equation (6) it follows that $\theta=78.8°$ with $\tan\theta=5.0$.

Using characteristic lines may result in high beam intensities, but putting restrictions on possible diffraction angles will limit hardware constructions. An alternative is to use the continuous Bremsstrahlung background spectrum of a tungsten target tube and choose a desired wavelength (by means of a monochromator). This way, the angle $\theta$ could be chosen as close to $\pi/2$ as the equipment construction allows. In addition, there would be no need to use any exotic X-ray tube target.

The monochromatic approach according to this invention needs either divergent or convergent incident beams. Convergent monochromatic beams can be realized using focussing monochromators (bent crystals).

Typical sampling times for diode detector arrays with 1024 channels are around 1 ms. However, the sampling time (inverse of sampling rate) depends on the X-ray beam intensity. Small intensities may result in larger sampling times. For this reason, use of a characteristic X-ray line might be the preferred choice (but this must not hold for characteristic lines of exotic targets in comparison to the Bremsstrahlung intensity of a tungsten target tube, for example). Sampling times from 1 ms up to a 1 second are reasonable.

With respect to temperature measurement resolution in the monochromatic approach, it is best to move the detector far away from the measurement spot on the semiconductor. However, there is always a trade-off between resolution and reflected beam intensity. If necessary, one might sacrifice resolution for a decreased data acquisition time and hence higher sampling rates. The sampling rate is not a problem for temperature measurements during isothermal processes, during steady states of rapid thermal processes, or in calibration applications.

In summary, in the described implementation of the invention, the measurement spot was chosen to be located at the backside of a silicon substrate wafer 24 at or near the center. The slightly divergent beam coming from the X-ray source 12 (sealed tube) was reflected by a bent monochromator crystal 26. The choice of monochromator crystal, reflection, and diffraction angles are determined in such a way that the monochromatic beam that reaches the wafer in the small measurement spot 28 has the desired wavelength. The use of a bent monochromator crystal 26 allows one to focus the outgoing monochromatic X-rays to the measurement spot 28. Out of the bundle of X-ray beams converging on the measurement spot under different incident angles, only those beams that satisfy the Bragg condition are reflected by the semiconductor wafer 24. As shown by the solid line in FIG. 1, only one particular beam fulfills this condition for a given temperature. The corresponding angle $\theta$ depends on the semiconductor lattice constant a(T) which is itself a function of substrate temperature T (thermal expansion). Measurement of the reflection angle $\theta$ using a fast multi-channel photo diode array detector therefore determines the semiconductor substrate temperature. Note that the (bent) monochromator 26 must be maintained at a definite temperature in order to avoid wavelength changes of the monochromatic X-rays being used. Also, the largest Bragg angle $\theta$ is obtained when the semiconductor substrate temperature is smallest. In accordance with Equation (10a), the higher the substrate temperature, the larger the lattice constant, according to Equation (7), and the smaller the Bragg angle.

While the invention has been described in terms of the embodiments described above, those skilled in the art will recognize that the invention can be practiced with modification within the spirit and scope of the appended claims.

Having thus described our invention, what we claim as new and desire to secure by Letters Patent is as follows:

1. A non-contact in-situ temperature measurement apparatus for a single crystal substrate such as a semiconductor wafer, comprising:

a process chamber housing the semiconductor wafer;

an incident X-ray source communicating with said wafer through a window in the process chamber;

a diode array detector for receiving reflected X-rays from said wafer; and means responsive to said diode array detector for determining the lattice constant and temperature of the wafer based on received reflected X-rays.

2. The apparatus of claim 1, further including a monochromator disposed between said X-ray source and said wafer to select a desired wavelength.

3. The apparatus of claim 2, wherein the monochromator is a bent monochromator for focusing the X-rays.

4. The apparatus of claim 1, wherein the incident X-ray source generates X-rays having a wavelength $\lambda_1$, said apparatus further comprising:

a second incident X-ray source communicating with said wafer through a window in the process chamber, said second incident X-ray source generating a reference beam of X-rays having a wavelength $\lambda_2$, where $\lambda_2 < \lambda_1$;

a second diode array detector for receiving reflected X-rays of wavelength $\lambda_2$ from said wafer; and means responsive to said first and second diode array detectors for determining a measurement of wafer position or movement.

5. The apparatus of claim 1, wherein the window is a beryllium window.

6. The apparatus of claim 1, further including positioning means for accurately registering the position of the wafer with respect to said diode array detector prior to a temperature measurement.

7. A method of non-contact in-situ temperature measurement for a semiconductor wafer, the method comprising the steps of:

providing a single crystal silicon wafer in a process chamber;

providing an incident X-ray source communicating with said wafer in the process chamber;

receiving reflected x-rays from said wafer;

determining the lattice constant of the wafer based on the received reflected x-ray; and obtaining the temperature of the wafer as determined by the lattice constant.

8. The method of claim 7, further including the step of accurately determining the position of the wafer prior to providing the X-rays.

9. The method of claim 8, further including a step of selecting a certain radiation wavelength from the X-ray source.

10. The method of claim 9, further including a step of focusing the selected wavelength on said wafer.

11. The method of claim 7, further including the step of selecting a certain diffraction angle.

12. The method of claim 11, further including the use of a collimated polychromatic X-ray source.

13. The method of claim 12, further including the measurement of the wavelength or wavelength shift of the diffracted X-ray.

* * * * *